United States Patent [19]
Binet et al.

[11] Patent Number: 5,614,534
[45] Date of Patent: Mar. 25, 1997

[54] DERIVATIVES OF β, β-DIMETHYL-4-PIPERIDINEETHANAMINE AS INHIBITORS OF THE CHOLESTEROL BIOSYNTHESIS

[75] Inventors: Jean Binet, Fontaine-les-Dijon; Soth Samreth, Longvic; Daniel de Fornel, Dijon, all of France

[73] Assignee: Fournier Industrie et Sante, Paris, France

[21] Appl. No.: 545,626

[22] PCT Filed: May 17, 1994

[86] PCT No.: PCT/FR94/00584

§ 371 Date: Oct. 30, 1995

§ 102(e) Date: Oct. 30, 1995

[87] PCT Pub. No.: WO94/26713

PCT Pub. Date: Nov. 24, 1994

[30] Foreign Application Priority Data

May 17, 1993 [FR] France .................................. 93 05915

[51] Int. Cl.$^6$ ..................... C07D 211/26; C07D 211/34; A61K 31/445

[52] U.S. Cl. ................. 514/315; 514/316; 514/317; 514/323; 514/326; 546/186; 546/187; 546/191; 546/201; 546/210; 546/232; 546/233; 546/246; 546/247

[58] Field of Search ....................... 546/186, 187, 546/191, 210, 233, 246, 247, 201, 232; 514/315, 316, 326, 317, 323

[56] References Cited

U.S. PATENT DOCUMENTS

| | | |
|---|---|---|
| 4,248,877 | 2/1981 | Rissi et al. ................ 514/327 |
| 4,473,694 | 9/1984 | Lai ........................... 546/247 |
| 4,569,933 | 2/1986 | Cornu et al. ............... 514/237 |
| 4,879,300 | 11/1989 | Giordani et al. .......... 514/317 |
| 4,939,161 | 7/1990 | Lalinde et al. ............ 514/326 |
| 5,246,945 | 9/1993 | Kikuchi et al. ........... 514/331 |

FOREIGN PATENT DOCUMENTS

| | | |
|---|---|---|
| 0420116 | 4/1991 | European Pat. Off. . |
| 0468457 | 1/1992 | European Pat. Off. . |
| 991509 | 5/1965 | United Kingdom . |

*Primary Examiner*—C. Warren Ivy
*Assistant Examiner*—Lyman H. Smith
*Attorney, Agent, or Firm*—Evenson, McKeown, Edwards & Lenahan, P.L.L.C.

[57] ABSTRACT

The present invention concerns β,β-dimethyl-4-piperidineethanamine compounds of the formula:

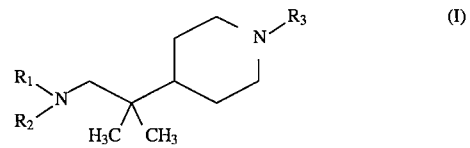

(wherein groups $R_1$ to $R_3$ are defined as indicated in the description), and addition salts thereof.

It also concerns a process for their preparation and their therapeutic use as inhibitors for the cholesterol biosynthesis, in particular as epoxysqualene cyclase inhibitors, for obtaining an as hypocholesterolemic, hypolipemic, antiatheromatic and/or antifungal drug.

10 Claims, No Drawings

DERIVATIVES OF β,β-DIMETHYL-4-PIPERIDINEETHANAMINE AS INHIBITORS OF THE CHOLESTEROL BIOSYNTHESIS

This application is a 35 U.S.C. 371 National Stage filing of PCT/FR94/00584 published as WO 94/26713 on Nov. 24, 1994.

FIELD OF THE INVENTION

The present invention concerns β,β-dimethyl-4-piperidineethanamine derivatives, as novel industrial products, which are inhibitors to the biosynthesis of cholesterol, in particular of epoxysqualene cyclase, in mammals and fungi. The invention also concerns a method for their preparation and their therapeutic use as hypocholesterolemic, hypolipemic, antiatheromatic and antifungal agents.

PRIOR ART

Many studies have shown (i) that there is a link between a high cholesterol level and the associated cardiovascular risks, and (ii) the importance of normalising this cholesterol level.

A number of compounds which inhibit biosynthesis of cholesterol have thus been developed, for example HGM-CoA reductase inhibitors.

It is preferable to inhibit this biosynthesis in its final stage since the first precursors can be involved in the synthesis of other biologically important molecules.

Research has therefore been carried out with the aim of developing epoxysqualene cyclase and squalene epoxydase inhibitors; these enzymes catalyse the transformation of squalene, via 2,3-oxydosqualene, to lanosterol which is the first compound to be formed in the sterol family.

Similarly, the biosynthesis of endogenous ergosterol is necessary for the growth and reproduction of certain fungi. Compounds which inhibit this biosynthesis, and inhibit in particular the two enzymes described above, thus have very important antifungal properties.

Some epoxysqualene cyclase inhibitors which can be used as inhibitors for cholesterol biosynthesis are already known.

Examples are International application WO-A-89/08450 and U.S. Pat. No. 5,084,461, which describe decaline and azadecaline derivatives, and patent application EP-A-0 468 434, which describes ethers or thioethers of 4-hydroxypiperidine. Patent applications EP-A-0 468 457 and EP-A-0 420 116 describe derivatives of β-methyl-4-piperidine ethanol and alkyl-4-piperidinol compounds for use as squalene epoxydase inhibitors and indicate their use as antiatheromatic and antifungal agents.

None of these prior art documents either describes or suggests (i) β,β-dimethyl-4-piperidineethanamine derivatives as products, and (ii) their use as inhibitors for the biosynthesis of cholesterol, and in particular as inhibitors of epoxysqualene cyclase.

OBJECT OF THE INVENTION

The present invention thus proposes β,β-dimethyl-4-piperidineethanamine derivatives which are inhibitors to the biosynthesis of cholesterol, and in particular inhibitors of epoxysqualene cyclase.

The present invention concerns compounds selected from the group consisting of β,β-dimethyl-4-piperidineethanamines with of the formula:

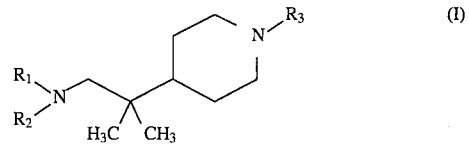

wherein $R_1$ and $R_2$, which may be identical or different, each represent a hydrogen atom, a $C_1$–$C_4$ alkyl group, a $C_2$–$C_5$ acyl group or a phenylmethyl group, or form a piperidinyl group with the nitrogen atom to which they are bonded, $R_3$ represents
  a linear or branched $C_1$–$C_{12}$ alkyl group which may be substituted by:
    a) an imidazolyl group, or
    b) a phenyl group which may itself be substituted by a linear or branched $C_1$–$C_4$ alkyl group,
  a linear or branched $C_3$–$C_{10}$ alkyl group comprising one or more C=C or C≡C bonds, and which may be substituted by a phenyl group,
  a linear or branched $C_1$–$C_4$ alkyloxy group, substituted by a para-chlorophenyl group,
  a —CO—$R_8$ group, wherein $R_8$ represents a linear or branched $C_8$–$C_{11}$ alkyl group which may be substituted by an imidazolyl group, a linear or branched $C_1$–$C_4$ alkyloxy group, substituted by a para-chlorophenyl group, or a linear or branched $C_2$–$C_4$ alkyl group comprising at least one double bond and substituted by a phenyl group,
  a linear or branched $C_1$–$C_4$ alkyl group substituted by one of the following groups:
    a —COOR$_4$ group, wherein $R_4$ represents either a hydrogen atom or a linear or branched $C_1$–$C_4$ alkyl group,
    a 1H-isoindole-1,3(2H)-dione group,
    a NR$_5$R$_6$ group, wherein $R_5$ and $R_6$, which may be identical or different, each represent a hydrogen atom or a linear or branched $C_1$–$C_4$ alkyl group,
    a —NH—CO—R$_7$ group or a —CO—NH—R$_7$ group wherein $R_7$ represents a linear or branched $C_1$–$C_6$ alkyl group, and their addition salts.

The invention also concerns a method for the preparation of compounds of the formula I, as described below.

DETAILED DESCRIPTION OF THE INVENTION

Preferred alkyl groups are methyl, ethyl, n-propyl, isopropyl, n-butyl, n-pentyl, t.-butyl, 2-methylpropyl, 5-methylpentyl, octyl, nonyl, decyl, undecyl and dodecyl groups.

Preferred $C_3$–$C_{10}$ alkyl groups comprising one or more C=C or C≡C bonds are 2-ethen-1-yl, 4-methyl-2-buten-1-yl and 6,6-dimethyl-hept-2-en-4-yn-1-yl groups.

The term addition salts here means acid and ammonium addition salts.

The term acid addition salts here means the salts obtained with organic acids such as 4-methylbenzene sulphonic acid, (E)-2-butenedioic acid, (Z)-2-butenedioic acid, ethanedioic acid, methane sulphonic acid, paratoluene sulphonic acid, acetic acid, citric acid, aspartic acid, glutamic acid, succinic acid, or propionic acid, or with inorganic acids such as hydrochloric acid, hydrobromic acid, sulphuric acid, nitric acid and phosphoric acid.

The term ammonium salts here means ammonium salts obtained by the reaction of a halogenated hydrocarbon, especially a $C_1$–$C_{14}$ hydrocarbon, in particular a halogenated alkyl compound such as methyl iodide, with a compound of the formula I in its base form.

Compounds of the formula (I) according to the invention can be prepared using a method which is characterised in that it comprises the following steps:

(i) N-alkylating or N-acylating a compound of the formula:

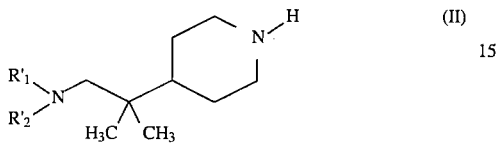

wherein:

$R'_1$ and $R'_2$, which may be identical or different, each represent a hydrogen atom, a $C_1$–$C_4$ alkyl group, or a phenylmethyl group, or form a piperidinyl group with the nitrogen atom to which they are bonded, by reaction with a compound of the formula $R'_3$—X wherein X represents a halogen such as a bromine or chlorine atom, and $R'_3$ represents:

a linear or branched $C_1$–$C_{12}$ alkyl group which may be substituted by an imidazolyl group or a phenyl group which may itself be substituted by a linear or branched $C_1$–$C_4$ alkyl group, a linear or branched $C_3$–$C_{10}$ alkyl group containing one or more C=C or C≡C bonds, a —CO—$R'_8$ group, wherein $R'_8$ represents a linear or branched $C_8$–$C_{11}$ alkyl group which may be substituted by an imidazolyl group, a linear or branched $C_1$–$C_4$ alkyl group substituted by a —COO$R'_4$ group, wherein $R'_4$ represents a hydrogen atom or a linear or branched $C_1$–$C_4$ alkyl group, a 1H-isoindole-1,3(2H)-dione group, in the presence or otherwise of a polar or non-polar and aprotic solvent such as acetonitrile, trichloromethane or N,N-dimethylformamide, in the presence or otherwise of an alkali metal salt such as potassium carbonate, potassium iodate or sodium iodide and in the presence or otherwise of a strong base such as N,N-diethylethanamine, in particular in the case of N-acylation, in a concentration ratio of 1 mole of compound of the formula II for 1.1 moles of compound of the formula $R'_3$—X, at a temperature of between 0° C. and 200° C. for a period of at least one hour (i.e. one hour to several days) to obtain a compound of the formula:

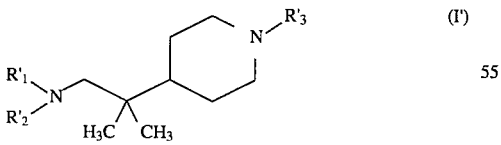

wherein $R'_1$, $R'_2$ and $R'_3$ are as defined above;

(ii) if necessary, carrying out at least one of the following treatments on the compounds of the formula I' thus obtained:

(a) transforming compounds of the formula I' wherein $R'_3$ represents a linear or branched $C_3$–$C_{10}$ alkyl group containing one or more C=C or C≡C bonds and $R'_1$ and $R'_2$ are as defined above, using methods which are known to the skilled person, in particular catalytic hydrogenation in a Parr's apparatus, in an alcohol such as methanol, in the presence of a catalyst such as palladium/charcoal, to compounds of the formula I wherein $R_1$ and $R_2$, which may be identical or different, each represent a hydrogen atom, a linear or branched $C_1$–$C_4$ alkyl group, or a phenylmethyl group, or form a piperidinyl group with the nitrogen atom to which they are bonded, and $R_3$ represents a linear or branched $C_3$–$C_{10}$ alkyl chain;

(b) hydrolysing compounds of the formula I' wherein $R'_1$ and $R'_2$ are as defined above and $R'_3$ represents a linear or branched $C_1$–$C_4$ alkyl group substituted by a 1H-isoindole-1,3(2H)-dione group, using methods which are known to the skilled person, in particular in the presence of hydrazine hydrate, optionally followed by N-alkylation of the primary amine thus produced, using an appropriate $C_1$–$C_4$ alkyl group to obtain compounds of the formula I wherein $R_1$ and $R_2$, which may be identical or different, each represent a hydrogen atom, a linear or branched $C_1$–$C_4$ alkyl group, or a phenylmethyl group, or form a piperidinyl group with the nitrogen atom to which they are bonded, and $R_3$ represents a linear or branched $C_1$–$C_4$ alkyl group substituted by a $NR_5R_6$ group wherein $R_5$ and $R_6$, which may be identical or different, each represent a hydrogen atom or a linear or branched $C_1$–$C_4$ alkyl group;

(c) N-acylating the primary amine obtained in step (b) using methods which are known to the skilled person, such as reaction with an acid halide of the formula X—CO—$R_7$ wherein X represents a halogen atom such as chlorine or bromine and $R_7$ represents a linear or branched $C_1$–$C_6$ alkyl group, to obtain compounds of the formula I wherein $R_1$ and $R_2$, which may be identical or different, each represent a hydrogen atom, a linear or branched $C_1$–$C_4$ alkyl group, or a phenylmethyl group, or form a piperidinyl group with the nitrogen atom to which they are bonded, and $R_3$ represents a linear or branched $C_1$–$C_4$ alkyl group substituted by a —NH—CO—$R_7$ group wherein $R_7$ represents a linear or branched $C_1$–$C_6$ alkyl group;

(d) amidifying compounds of the formula I' wherein $R'_1$ and $R'_2$ are as defined above and $R'_3$ represents a linear or branched $C_1$–$C_4$ alkyl group substituted by a —COO$R'_4$ group, wherein $R'_4$ represents a hydrogen atom or a linear or branched $C_1$–$C_4$ alkyl group, by reaction with an appropriate primary amine using methods which are known to the skilled person, to obtain compounds of the formula I wherein $R_1$ and $R_2$, which may be identical or different, each represent a hydrogen atom, a linear or branched $C_1$–$C_4$ alkyl group, or a phenylmethyl group, or form a piperidinyl group with the nitrogen atom to which they are bonded, and $R_3$ represents a linear or branched $C_1$–$C_4$ group substituted by a —CO—NH—$R_7$ group wherein $R_7$ represents a linear or branched $C_1$–$C_6$ alkyl group;

(e) reducing compounds of the formula I' wherein $R'_1$ and $R'_2$ are as defined above and $R'_3$ represents a —CO—$R'_8$ group, wherein $R'_8$ represents a linear or branched $C_8$–$C_{11}$ alkyl group which may be substituted by an imidazolyl group, using methods which are known to the skilled person, in the presence of a reducing agent such as an aluminium hydride derivative, then treating with a strong base such as sodium hydroxide to obtain compounds of the formula I wherein $R_1$ and $R_2$, which may be identical or different, each represent a hydrogen atom, a $C_1$–$C_4$ alkyl group, or a phenylmethyl group, or form a piperidinyl group with the nitrogen atom to which they are bonded, and $R_3$ represents a linear or branched $C_8$–$C_{12}$ alkyl group which may be substituted by an imidazolyl group;

(f) acylating compounds of the formula I' wherein one of the two groups $R'_1$ and $R'_2$ represent a hydrogen atom, the other being a hydrogen atom, a $C_1$–$C_4$ alkyl group or a phenylmethyl group, and $R'_3$ has the meaning given for $R_3$, using methods which are known to the skilled person, in particular by reacting with an acid anhydride such as acetic anhydride, to produce compounds of the formula I wherein one of the groups $R_1$ or $R_2$ represents an acyl group, the other being a hydrogen atom, a $C_1$–$C_4$ alkyl group or a phenylmethyl group, and $R_3$ represents a linear or branched $C_1$–$C_{12}$ alkyl group which may be substituted by an imidazolyl group or a phenyl group which may itself be substituted by a $C_1$–$C_4$ alkyl group, a linear or branched $C_3$–$C_{10}$ alkyl group containing one or more C=C or C≡C bonds, a —CO—$R_8$ group wherein $R_8$ represents a linear or branched $C_8$–$C_{11}$ alkyl group which may be substituted by an imidazolyl group, a linear or branched $C_1$–$C_4$ alkyl group substituted by:
a —COOR$_4$ group wherein $R_4$ represents a hydrogen atom or a linear or branched $C_1$–$C_4$ alkyl group,
a 1H-isoindole-1,3(2H)-dione group,
a NR$_5$R$_6$ group wherein $R_5$ and $R_6$, which may be identical or different, each represent a hydrogen atom or a linear or branched $C_1$–$C_4$ alkyl group,
a —NH—CO—R$_7$ or —CO—NH—R$_7$ group wherein $R_7$ represents a linear or branched $C_1$–$C_6$ alkyl group.

The term halogen atom here means fluorine, bromine, chlorine and iodine atoms; preferred halogen atoms are chlorine and bromine for the synthesis and iodine for the ammonium salts.

It is recommended that compounds of the formula II wherein $R'_1$ and $R'_2$ are as defined above are prepared using the Mannich reaction to prepare β,β-dimethyl-4-pyridineethanamine derivatives of the formula:

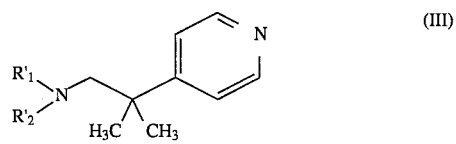

wherein $R'_1$ and $R'_2$, which may be identical or different, each represent a hydrogen atom, a $C_1$–$C_4$ alkyl group, or a phenylmethyl group, or form a piperidinyl group with the nitrogen atom to which they are bonded, using methods which are known to the skilled person, in particular by reacting (1-methylethyl)-4-pyridine, in solution in acetic acid and in the presence of formaldehyde, with an appropriate amine, then hydrogenating the compounds of the formula III thus produced, using methods which are known to the skilled person, in particular by catalytic hydrogenation in a Parr's apparatus, in solution in a solvent such as acetic acid, in the presence of a catalyst such as platinum dioxide.

Compounds of the formula II and intermediate compounds of the formula III, wherein $R'_1$ and $R'_2$, which may be identical or different, each represent a hydrogen atom, a $C_1$–$C_4$ alkyl group, or a phenylmethyl group, or form a piperidinyl group with the nitrogen atom to which they are bonded, are novel compounds.

A further method in accordance with the invention produces compounds of the formula I', wherein $R'_1$ and $R'_2$, which may be identical or different, each represent a hydrogen atom, a $C_1$–$C_4$ alkyl group, or a phenylmethyl group, or form a piperidinyl group with the nitrogen atom to which they are bonded, and $R'_3$ represents a linear or branched $C_1$–$C_{12}$ alkyl group or a linear or branched $C_3$–$C_{10}$ alkyl group containing one or more C=C or C≡C bonds, using methods which are known to the skilled person, by reducing the corresponding α,α-dimethyl-4-piperidine acetamide derivative of the formula:

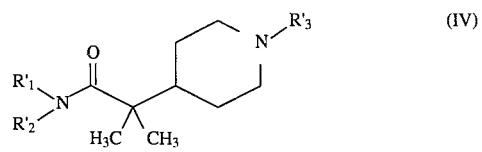

in particular by agitation for one to three hours at room temperature (15° C.–25° C.), in an appropriate solvent such as methylbenzene, for example, in the presence of a reducing agent such as bis(2-methoxyethoxy) aluminium-sodium hydride, with a molar ratio of one mole of α,α-dimethyl-4-piperidine acetamide for 0.4 to 0.5 mole of reducing agent, and refluxing the mixture for between one hour and several hours.

Compounds of the formula IV are produced in a first step by aldolising a 4-piperidone derivative of the formula:

wherein Z represents a protective group such as phenylmethyl, 4-methoxyphenylmethyl or COOY groups wherein Y represents a $C_1$–$C_4$ alkyl group or a phenylmethyl group, with a compound of the formula $(CH_3)_2$—CH—$CO_2$—W wherein W represents a $C_1$–$C_4$ alkyl group, using methods which are known to the skilled person, in particular by reaction in an anhydrous and aprotic solvent such as tetrahydrofuran, for example, at a temperature of −70° C., to obtain a compound of the formula:

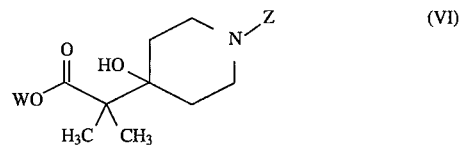

wherein Z and W are as defined above, then dehydrating the compound of the formula VI using methods which are known to the skilled person, in particular by reaction with thionyl chloride in a halogenated solvent and treatment with a strong base such as sodium hydroxide, to form a corresponding derivative of α,α-dimethyl-1,2,3,6-tetrahydro-4-pyridine acetic acid of the formula:

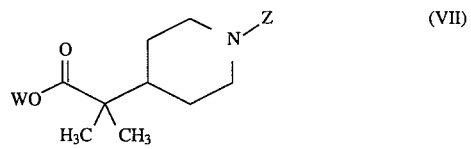

The compounds of the formula VII are then deprotected and hydrogenated using methods which are known to the skilled person, in particular by hydrogenation in a Parr's apparatus, in solution in an alcohol such as ethanol, for example, in the presence of a catalyst such as palladium/charcoal, for example, to obtain compound of the formula:

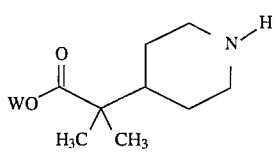

(VIII)

wherein W represents a $C_1$–$C_4$ alkyl group.

The piperidine derivative of the formula VIII which is thus obtained is then N-alkylated, using methods which are known to the skilled person, by reaction in a polar solvent such as acetonitrile, for example, with an appropriate halogenated derivative such as a brominated derivative, for example, to obtain a compound of the formula:

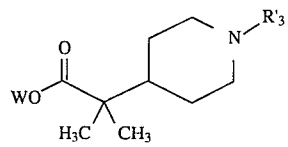

(IX)

wherein W is as defined above and $R'_3$ represents a linear or branched $C_1$–$C_{12}$ alkyl group or a linear or branched $C_3$–$C_{10}$ alkyl group containing one or more C=C or C≡C bonds.

Saponification of the above compounds of the formula IX, using methods which are known to the skilled person, in particular by reaction with a strong base such as sodium or potassium hydroxide, for example, in an alcohol such as ethanol, for example, produces the corresponding $\alpha,\alpha$-dimethyl-4-piperidine acetic acid which is amidified using an appropriate amine according to methods which are known to the skilled person, in particular by reaction in the presence of thionyl chloride in a halogenated solvent such as trichloromethane, for example, to obtain the desired $\alpha,\alpha$-dimethyl-4-piperidine acetamide compounds of the formula IV.

Intermediate compounds of the formula IV, wherein $R'_1$ and $R'_2$, which may be identical or different, each represent a hydrogen atom, a linear or branched $C_1$–$C_4$ alkyl group, or a phenylmethyl group, or form a piperidinyl group with the nitrogen atom to which they are bonded, and $R'_3$ represents a linear or branched $C_1$–$C_{12}$ alkyl group or a linear or branched $C_3$–$C_{10}$ alkyl group containing one or more C=C or C≡C bonds, are novel compounds and constitute one of the objects of the invention.

Intermediate compounds of the formula IX, wherein W represents a hydrogen atom or a $C_1$–$C_4$ alkyl group and $R'_3$ represents a linear or branched $C_1$–$C_{12}$ alkyl group or a linear or branched $C_3$–$C_{10}$ alkyl group containing one or more C=C or C≡C bonds, are novel, with the exception of the compound wherein W and $R'_3$ both represent a methyl group.

Similarly, intermediate derivatives of the formulae VI and VII, wherein W represents a linear or branched $C_1$–$C_4$ alkyl group and Z represents a protective group such as a phenylmethyl group, a 4-methoxyphenylmethyl group or a COOY group wherein Y represents a $C_1$–$C_4$ alkyl group or a phenylmethyl group, for example, are novel compounds.

Intermediate compounds of the formula VIII, wherein W represents a linear or branched $C_1$–$C_4$ alkyl group, are novel compounds.

The invention will be better understood from the following preparation examples. These examples illustrate the invention without limiting its scope. For convenience, the examples under the heading "Preparations" refer to the preparation of precursors and intermediates, and the "Examples" refer to the preparation of the products of the formula I according to the invention.

PREPARATION I

Preparation of 1-phenylmethyl-$\alpha,\alpha$-dimethyl-4-hydroxy-4-piperidine-acetic Acid Ethyl Ester 125 ml of 1.6M butyllithium was added dropwise to a solution of 18.5 g (0.18 mole) of N-(1-methylethyl)-2-propanamine in 75 ml of tetrahydrofuran, cooled to a temperature of –70° C. The mixture was stirred for ten minutes at this temperature then 17.5 g (0.15 mole) of 2-methyl-propanoic acid ethyl ester in solution in 70 ml of tetrahydrofuran was added, keeping the temperature at –70° C. After stirring for one hour at this temperature, a solution of 26 g (0.14 mole) of 1-phenylmethyl-4-piperidinone in 70 ml of tetrahydrofuran was added. The reaction medium was stirred for 1.5 h at a temperature of –70° C. and was then allowed to return to room temperature. After evaporating off the solvents under reduced pressure, the residue was poured into a saturated solution of ammonium chloride. The organic phase was extracted with ether, washed with water, dried over magnesium sulphate and filtered and the solvents were evaporated off under reduced pressure. After purification by distillation, 32 g (yield: 76%) of the desired product was obtained as an oil. B Pt=145°–150° C. (0.05 mm Hg, i.e. about 6.66 Pa)

PREPARATION II

Preparation of the Hydrochloride of 1-phenylmethyl-$\alpha,\alpha$-dimethyl-1,2,3,6-tetrahydro-4-pyridine-acetic Acid Ethyl Ester 24 ml ($33.10^{-2}$ mole) of thionyl chloride was added dropwise to a solution of 50 g ($16.4 \times 10^{-2}$ mole) of 1-phenylmethyl-$\alpha,\alpha$-dimethyl-4-hydroxy-4-piperidine-acetic acid ethyl ester in 200 ml of trichloromethane and in the presence of 0.5 ml of N,N-dimethylformamide. The reaction mixture was refluxed for 18 hours then cooled. The solvents were evaporated off under reduced pressure and the residue was taken up in an aqueous solution of 20 ml of 10N sodium hydroxide. The aqueous phase was extracted with ether. The organic phase was washed with brine, dried over magnesium sulphate and filtered and the solvents were evaporated off under reduced pressure. An oil was obtained which was taken up in 300 ml of 2-propanol and gaseous HCl was bubbled into the solution obtained until the pH was acidic. The precipitate was filtered and recrystallised from 2-propanol. 38.9 g (yield: 74%) of the desired product was obtained. M Pt=208° C.

PREPARATION III

Preparation of $\alpha,\alpha$-dimethyl-4-piperidine-acetic Acid Ethyl Ester

A solution of 246 g ($76.6 \times 10^{-2}$ mole) of the hydrochloride of 1-phenylmethyl-$\alpha,\alpha$-dimethyl-1,2,3,6-tetrahydro-4-pyridine-acetic acid ethyl ester in 1.5 liters of ethanol was hydrogenated in a Parr's apparatus at 50° C. at a hydrogen pressure of $3.10^6$ Pa in the presence of 20 g of 5% palladium/charcoal. After filtering, the filtrate obtained was evaporated off under reduced pressure. The residue obtained was taken up in water and rendered alkaline with 500 ml of 5N sodium hydroxide. It was extracted with ethyl acetate. The organic phase was dried over magnesium sulphate and filtered and the solvents were evaporated off under reduced pressure. 125.3 g (yield: 82%) of the desired product was obtained as an oil. $n^{21}=1.47$

PREPARATION IV

Preparation Ethyl Ester of 1-dodecyl-α,α-dimethyl-piperidine Acetic Acid, (E)-2-butenedioate A mixture of 27 g (0.135 mole) of the ethyl ester of α,α-dimethyl-piperidine-acetic acid, 42.2 g (0.169 mole) of 1-bromododecane and 46.8 g (0.339 mole) of potassium bicarbonate in 250 ml of acetonitrile was refluxed for 5.5 hours. After pouring the mixture onto ice, the organic phase was extracted with ethyl acetate, washed with water, dried and filtered and the solvents were evaporated off under reduced pressure. After purification by silica gel chromatography, eluting with 9/1 (v/v) hexane/2-propanone, 33.9 g (yield: 68%) of the ethyl ester of 1-dodecyl-α,α-dimethyl-4-piperidine acetic acid was obtained as an oil. The desired fumarate was prepared from this oil. M Pt=106° C.

PREPARATION V

Preparation of the Hydrochloride of 1-dodecyl-α,α-dimethyl-4-piperidine-acetic Acid 24.6 g ($61.4 \times 10^{-2}$ mole) of sodium hydroxide pellets were added to a solution of 22.5 g ($6.10^{-2}$ mole) of the ethyl ester of 1-dodecyl-α,α-dimethyl-4-piperidine acetic acid in 210 ml of a 2/1 (v/v) ethanol/water mixture and the reaction mixture was refluxed for 72 hours. It was then poured into 200 ml of 5N hydrochloric acid. The precipitate obtained was filtered and washed with ether. After recrystallisation from a 2/8 (v/v) ethanol/water mixture, 17.6 g (yield: 78%) of the desired product was obtained. M Pt=192° C.

PREPARATION VI

Preparation of 1-dodecyl-α,α-dimethyl-4-piperidine-acetamide

A solution of 8.4 g ($2.2 \times 10^{-2}$ mole) of the hydrochloride of 1-dodecyl-α,α-dimethyl-4-piperidine-acetic acid in 50 ml of thionyl chloride was refluxed for 8 hours. After evaporating off the solvents under reduced pressure, the residue was dissolved in a 2/1 (v/v) methylbenzene/trichloromethane mixture and then cooled. 60 ml of liquid ammonia was then carefully added and the solution was left at room temperature for 72 hours. The mixture was poured into water and extracted with ethyl acetate. The organic phase was washed with water and dried over magnesium sulphate and the solvents were evaporated off under reduced pressure. The product obtained was purified using silica gel chromatography, eluting with a 9/1/0.05 (v/v/v) acetic acid/methanol/ammonia mixture. 5.2 g (yield: 69%) of the desired product, recrystallised from diisopropyl ether, was obtained. M Pt=123° C.

The following compounds were prepared in an analogous manner to the above synthesis:

1-dodecyl-N,N,α,α-tetramethyl-4-piperidine-acetamide, (E)-2-butene-dioate, by replacing the ammonia with N-methyl methanamine; M Pt=190° C.

1-dodecyl-N-phenylmethyl-N,α,α-trimethyl-4-piperidine-acetamide, ethanedioate, by replacing the ammonia with N-phenylmethylmethanamine; M Pt=121°–128° C.

1-dodecyl-α,α-dimethyl-N,N-diethyl-4-piperidine-acetamide, by replacing the ammonia with N,N-diethylamine; M Pt=50° C.

1-dodecyl-N-phenylmethyl,α,α-dimethyl-4-piperidine-acetamide, by replacing the ammonia with phenylmethylamine; M Pt=74° C.

1-dodecyl-N,α,α-trimethyl-4-piperidine-acetamide, by replacing the ammonia with methylamine; M Pt=78° C.

1-dodecyl-N-propyl-α,α-dimethyl-4-piperidine-acetamide, by replacing the ammonia with propanamine; M Pt=72°–75° C.

1-dodecyl-N-(1-methylethyl)-α,α-dimethyl-4-piperidine-acetamide, by replacing the ammonia with 1-methylethanamine; M Pt=68° C.

1-dodecyl-n-ethyl-α,α-dimethyl-4-piperidine-acetamide, by replacing the ammonia with ethanamine; M Pt=67° C.

EXAMPLE b 1

Preparation of 1-dodecyl-β,β-dimethyl-4-piperidineethanamine, (E)-2-butenedioate.

10 ml of bis(2-methoxyethoxy)aluminium-sodium hydride was added dropwise to a solution of 2.95 g ($8.7 \times 10^{-2}$ mole) of 1-dodecyl-α,α-dimethyl-4-piperidine-acetamide in 80 ml of methylbenzene. After stirring for one hour at room temperature, the mixture was refluxed for three hours. After cooling the mixture, 50 ml of 3N sodium hydroxide was carefully added and stirring was continued for 24 hours. The resulting mixture was extracted with methylbenzene. The organic phase was washed with water, dried over magnesium sulphate and filtered and the solvents were evaporated off under reduced pressure. The product was purified using silica gel chromatography, eluting with a 4/1/0.1 (v/v/v) ethyl acetate/methanol/ammonia mixture. 1.8 g (yield: 64%) of 1-dodecyl-β,β-dimethyl-4-piperidineethanamine was obtained as an oil. The (E)-2-butenedioate was obtained from this oil in an acetone-ether mixture. M Pt=100°–120° C.

The following products were obtained using the method of Example 1 and analogous derivatives to 1-dodecyl-α,α-dimethyl-4-piperidine-acetamide, as prepared above:

EXAMPLE 2

1-dodecyl-N,N,β,β-tetramethyl-4-piperidineethanamine, (E)-2-butenedioate. M Pt=130° C.

EXAMPLE 3

1-dodecyl-N-phenylmethyl-N,β,β-trimethyl-4-piperidineethanamine, (E)-2-butenedioate. M Pt=124°–125° C.

EXAMPLE 4

1-dodecyl-N,N-diethyl,β,β-dimethyl-4-piperidineethanamine, (E)-2-butenedioate. M Pt=110°–115° C.

EXAMPLE 5

1-dodecyl-N-phenylmethyl,β,β-dimethyl-4-piperidineethanamine, (E)-2-butenedioate. M Pt=175°–177° C.

EXAMPLE 6

1-dodecyl-N,β,β-trimethyl-4-piperidineethanamine, 4-methylbenzene sulphonate. M Pt=139° C.

EXAMPLE 7

1-dodecyl-N-propyl,β,β-dimethyl-4-piperidineethanamine, ethanedioate. M Pt=186°–188° C.

EXAMPLE 8

1-dodecyl-N-(1-methylethyl)-β,β-dimethyl-4-piperidineethanamine, 4-methylbenzene sulphonate. M Pt=115°–118° C.

EXAMPLE 9

1-dodecyl-N-ethyl,β,β-dimethyl-4-piperidineethanamine, (E)-2-butenedioate. M Pt=135°–157° C.

EXAMPLE 10

Preparation of N-methyl-N-[2-methyl-2-[(1-dodecyl)-4-piperidinyl]propyl]acetamide, 4-methylbenzene Sulphonate 3.4 ml ($3.6 \times 10^{-2}$ mole) of acetic anhydride was added to a solution of 8 g ($2.4 \times 10^{-2}$ mole) of 1-dodecyl-N,β,β-trimethyl-4-piperidineethanamine in 100 ml of dichloromethane and 16.8 ml of N,N-diethylethanamine. The reaction mixture was stirred for 12 hours at room temperature. The solution was poured into a 1N sodium hydroxide solution and extracted with trichloromethane. The organic phase was washed with water, dried and filtered and the solvents were evaporated off under reduced pressure. 8.7 g of N-methyl-N-[2-methyl-2-[(1-dodecyl)-4-piperidinyl]propyl]acetamide (yield: 97%) was obtained, from which the 4-methylbenzene sulphonate was prepared and recrystallised from ethyl acetate. M Pt=102°–103° C.

The following compound was produced using an analogous method, starting with 1-dodecyl-β,β-dimethyl-4-piperidineethanamine:

EXAMPLE 11

N-[2-methyl-2-[(1-dodecyl)-4-piperidinyl]propyl]-N-acetamide, (E)-2-butenedioate M Pt=125° C.

PREPARATION VII

Preparation of N,N,β,β-tetramethyl-4-pyridineethanamine 300 ml (2.5 moles) of N,N-dimethylamine was added dropwise to a solution of 100 g ($82.5 \times 10^{-2}$ mole) of (1-methylethyl)-4-pyridine in 800 ml of acetic acid and 200 ml of an aqueous 37% formaldehyde solution. The mixture was refluxed for 72 hours. 100 ml of an aqueous 37% formaldehyde solution and 150 ml of N,N-dimethylamine were added and refluxing was continued, with stirring, for 24 hours. The solvents were evaporated off under reduced pressure and the residue was taken up in an aqueous 30% sodium hydroxide solution. This was extracted with ethyl acetate. The organic phase was washed with water, dried over magnesium sulphate and filtered and the solvents were evaporated off under reduced pressure. 70.5 g of the desired product (yield: 49%) was recovered as an oil. B Pt=50° C. under 0.05 mm Hg (i.e. about 6.66 Pa)

4-[[1-(1-piperidinyl)-2-methyl]propyl]pyridine, (E)-2-butene-dioate was prepared using an analogous method to the above synthesis, replacing the N,N-dimethylamine with piperidine. M Pt=160° C.

PREPARATION VIII

Preparation of N,N,β,β-tetramethyl-4-piperidineethanamine

A solution of 2 g ($1.1 \times 10^{-2}$ mole) of N,N,β,β-tetramethyl-4-pyridineethanamine in 400 ml of acetic acid was hydrogenated in a Parr's apparatus at 50° C. at a hydrogen pressure of $3.10^6$ Pa in the presence of platinum dioxide. After eliminating the catalyst by filtering, the solvents were evaporated off under reduced pressure. The residue obtained was taken up in an aqueous 30% sodium hydroxide solution and extracted with methylene chloride. The organic phase was washed, dried over magnesium sulphate and filtered and the solvents were evaporated off under reduced pressure. 1.9 g (yield: 92%) of the desired compound was obtained as an oil. B Pt=60°–64° C. under 0.02 mm Hg (i.e. about 2.66 Pa)

1-[2-(4-piperidinyl)-2-methyl]propyl]piperidine was prepared using the same method, starting from 4-[[1-(1-piperidinyl)-2-methyl]propyl]pyridine. B Pt=98°–100° C. under 0.02 mm Hg (i.e. about 2.66 Pa)

EXAMPLE 2 (FURTHER SYNTHESIS ROUTE)

Preparation of 1-dodecyl-N,N,β,β-tetramethyl-4-piperidineethanamine, (E)-2-butenedioate A mixture of 13 g ($7.10^{-2}$ mole) of N,N,β,β-tetramethyl-4-piperidineethanamine, 19.7 g ($7.9 \times 10^{-2}$ mole) of 1-bromododecane, 24.4 g ($17.6 \times 10^{-2}$ mole) of potassium carbonate and 0.5 g of potassium iodide in 150 ml of acetonitrile was refluxed for 12 hours.

After pouring the reaction mixture into water, it was extracted with ethyl acetate. The organic phase was washed with water, dried over magnesium sulphate and filtered, and the solvents were evaporated off under reduced pressure. The (E)-2-butanedioate was prepared in ethanol. 23.6 g (yield: 51%) of the desired product was obtained after recrystallisation from a 95/5 (v/v) 2-propanol/water mixture. M Pt=130° C.

The following products were prepared in analogous manner to the above synthesis:

EXAMPLE 12

N,N,β,β,1-pentamethyl-4-piperidineethanamine, (E)-2-butene-dioate. M Pt=194°–195° C.

EXAMPLE 13

1-(2-propenyl)-N,N,β,β-tetramethyl-4-piperidineethanamine, (Z)-2-butenedioate. M Pt=147° C.

EXAMPLE 14

1-(3,3-dimethylpropen-2-yl)-N,N,β,β-tetramethyl-4-piperidineethanamine, (E)-2-butenedioate. M Pt=184° C.

EXAMPLE 15

1-[[2-[4-(1-dodecylpiperidinyl)]-2-methyl]propyl]piperidine, (Z)-2-butenedioate. M Pt=129° C.

EXAMPLE 16

Preparation of (E)-1-(6,6-dimethyl-2-hepten-4-yn-1-yl)-N,N,β,β-tetramethyl-4-piperidineethanamine, (Z)-2-butenedioate 12 g ($6.10^{-2}$ mole) of 1-bromo-6,6-dimethyl-2-hepten-4-yne (E/Z=3/1) in solution in 20 ml of N,N-dimethylformamide was added drop-wise to a mixture of 10 g ($5.4 \times 10^{-2}$ mole) of N,N,β,β-tetramethyl-4-piperidineethanamine and 14.9 g of potassium carbonate in 150 ml of N,N-dimethylformamide. The mixture was stirred for 48 hours at room temperature then poured into water. This was extracted several times with ethyl acetate. The organic phase was washed with water, dried over magnesium sulphate and filtered and the solvents were evaporated off under reduced pressure. The residual oil obtained was purified by silica column chromatography, eluting with a 9/1 (v/v) methylene chloride/methanol mixture. After evaporation of the solvents under reduced pressure, 10.3 g (yield: 56%) of (E)-1-(6,6-dimethyl-2-hepten-4-yn-1-yl)-N,N,β,β-tetramethyl-4-piperidineethanamine was obtained. The corresponding (Z)-2-butene-dioate was obtained from this in ethanol. M Pt=185°–188° C.

EXAMPLE 17

Preparation of 1-(6,6-dimethyl-heptyl)-N,N,β,β-tetramethyl-4-piperidineethanamine, (E)-2-butenedioate 4.5 g ($1.5 \times 10^{-2}$ mole) of 1-(6,6-dimethyl-2-hepten-4-yn-1-yl)-N,N,β,β-tetramethyl-4-piperidineethanamine in solution in 150 ml of methanol, as a mixture of isomers, wherein the E/Z ratio was 3/1, was hydrogenated in a Parr's apparatus at 40° C., at a hydrogen pressure of $3.10^5$ Pa in the presence of 0.5 g of palladium/charcoal. When the reaction had finished, the catalyst was eliminated by filtering and the solvents were evaporated off under reduced pressure. 3.8 g (yield: 84%) of product was obtained as an oil. The (E)-2-butenedioate was prepared from this oil in ethanol. M Pt=161°–166° C.

EXAMPLE 18

Preparation of 1-[3-[4-(methylethyl)phenyl]-2-methyl-propyl]-N,N,β,β-tetramethyl-4-piperidineethanamine, (E)-2-butenedioate 7.6 g ($4.10^{-2}$ mole) of 2-methyl-3-[4-(methylethyl)phenyl]propanol and 5.1 g of sodium sulphate were added to a solution of 6.7 g ($3.6 \times 10^{-2}$ mole) of N,N,β,β-tetramethyl-4-piperidineethanamine in 100 ml of methanol. After addition of acetic acid to adjust the pH of the mixture to 6.5, 2.6 g ($4.10^{-2}$ mole) of sodium cyanoborohydride was added and the reaction mixture was stirred for 32 hours. After filtering and evaporating off the solvents, the residue was taken up in a sodium hydroxide 1N solution. It was extracted with ether. The organic phase was washed with water, dried and filtered and the solvents were evaporated off under reduced pressure.

The product obtained was purified using silica column chromatography, eluting with a methylene chloride/methanol mixture. 5 g (yield: 40%) of a product was recovered as an oil. The (E)-2-butenedioate was prepared from this oil in ethanol. M Pt=146°–150° C.

PREPARATION IX

Preparation of 1-(11-bromoundecanoyl)-N,N,β,β-tetramethyl-4-piperidineethanamine 17.5 g ($6.2 \times 10^{-2}$ mole) of the chloride of 11-bromoundecanoic acid diluted in 100 ml of trichloromethane was added dropwise to a solution of N,N,β,β-tetramethyl-4-piperidineethanamine in 120 ml of trichloromethane and 19.2 ml ($14.7 \times 10^{-2}$ mole) of N,N-diethylethanamine, cooled to 0° C. The reaction mixture was stirred for 3 hours at 0° C. then for 20 hours at room temperature. The reaction mixture was poured into water and allowed to settle. The organic phase was recovered and dried over magnesium sulphate and the solvents were evaporated off under reduced pressure. 12 g (yield: 57%) of the desired product was obtained as an oil.

The following product was obtained in the same manner starting from the chloride of undecanoic acid:

EXAMPLE 19

1-undecanoyl-N,N,β,β-tetramethyl-4-piperidineethanamine, ethanedioate. M Pt=134° C.

EXAMPLE 20

Preparation of 1-[(11-imidazolyl)undecanoyl]-N,N,β,β-tetramethyl-4-piperidineethanamine, Ethanedioate 1.8 g ($2.6 \times 10^{-2}$ mole) of imidazole was added to a suspension of 0.62 g of 60% sodium hydride in 200 ml of N,N-dimethylformamide and stirred for one hour at room temperature. 11 g ($2.5 \times 10^{-2}$ mole) of 1-(11-bromodecanoyl)-N,N,β,β-tetramethyl-4-piperidineethanamine oil obtained as above was added, diluted in 100 ml of N,N-dimethylformamide and the mixture was heated to 90° C. for 4 hours. After evaporation of the solvents, the residue was taken up in water. It was extracted with water and the organic phase was washed with water, dried and filtered and the solvents were evaporated off under reduced pressure. After purification by silica column chromatography, eluting with a 9/1 (v/v) methylene chloride/methanol mixture, 6 g (yield: 57%) of a product was obtained as an oil. The ethanedioate was prepared from this oil in acetone. M Pt=75°–80° C.

EXAMPLE 21

Preparation of 1-[(11-imidazolyl)undecyl]-N,N,β,β-tetramethyl-4-piperidineethanamine, (E)-2-butenedioate 10.5 ml ($3.8 \times 10^{-2}$ mole) of bis-(2-methoxyethoxy)aluminium-sodium hydride was added dropwise to a solution of 4 g ($0.9 \times 10^{-2}$ mole) of 1-undecanoyl-N,N,β,β-tetramethyl-4-piperidineethanamine in 120 ml of methylbenzene. The reaction :mixture was refluxed for 4 hours. 100 ml of a 3N sodium hydroxide solution was then added dropwise and the mixture was stirred for 24 hours at room temperature. It was extracted with methylbenzene. The organic phase was washed with a normal sodium hydroxide solution and then with water, dried and filtered and the solvents were evaporated off under reduced pressure. 2.8 g (yield: 74%) of 1-[(11-imidazolyl)undecyl]-N,N,β,β-tetramethyl-4-piperidineethanamine was obtained as an oil. The (E)-2-butenedioate was prepared from this oil in ethanol. M Pt=105°–110° C.

EXAMPLE 22

Preparation of 2-[[4-[2-(1-dimethylamino-2-methyl)propyl]-1-piperidinyl]propyl]-1H-isoindole-1,3(2H)-dione, (E)-2-butenedioate A mixture of 15 g ($8.10^{-2}$ mole) of N,N,β,β-tetramethyl-4-piperidineethanamine, 24 g ($9.10^{-2}$ mole) of 2-(3-bromopropyl)-1H-isoindole-1,3(2H)-dione, 28 g of potassium carbonate and some crystals of sodium iodide in 150 ml of acetonitrile was refluxed for 5 hours. After pouring the reaction mixture into water, it was extracted with ethyl acetate. The organic phase was washed with water, dried over magnesium sulphate and filtered and the solvents were evaporated off under reduced pressure. The residue from evaporation was purified by silica column chromatography, eluting with a 99/1 (v/v) ethyl acetate/methanol mixture. 5.9 g of 2-[[4-[2-(1-dimethylamino-2-methyl)propyl]-1-piperidinyl]propyl]-1H-isoindole-1,3(2H)-dione was recovered as an oil. The (E)-2-butenedioate was prepared from this oil in ethanol. M Pt=124° C.

EXAMPLE 23

Preparation of 1-[1-(3-aminopropyl)]-N,N,β,β-tetramethyl-4-piperidineethanamine, (E)-2-butenedioate A solution of 14 g ($3.8 \times 10^{-2}$ mole) of 2-[[4-[2-(1-dimethylamino-2-methyl)propyl]-1-piperidinyl]propyl]-1H-isoindole-1,3(2H)-dione in 100 ml of 95% ethanol and 4 ml of hydrazine hydrate was refluxed. The mixture was poured into a 5N sodium hydroxide solution and extracted with ethyl acetate. The organic phase was washed with water, dried over magnesium sulphate, filtered and the solvents were evaporated off under reduced pressure. 7.9 g (yield: 86%) of 1-[1-(3-aminopropyl)]-N,N,β,β-tetramethyl-4-piperidineethanamine was obtained as a yellow oil. The (E)-2-butenedioate was prepared from this oil in ethanol. M Pt=189°–191° C.

EXAMPLE 24

Preparation of N-[[4-[2-(1-dimethylamino-2-methyl)propyl]-1-piperidinyl]-1-propyl]-5-methylhexanamide, Ethanedioate 4.2 g ($1.7 \times 10^{-2}$ mole) of 1-[1-(3-aminopropyl)]-N,N,β,β-tetramethyl-4-piperidineethanamine was dissolved in 50 ml of methylene chloride and 12 ml of N,N-diethylethanamine. The solution was cooled to 0° C. and 2.6 g ($1.7 \times 10^{-2}$ mole) of 5-methylhexanoic acid chloride in solution in 25 ml of methylene chloride was added. The temperature of the mixture was allowed to return to 20° C. and stirring was continued for 12 hours at this temperature. The mixture was poured into water and extracted with methylene chloride. The organic phase was washed with water, dried over magnesium sulphate and filtered and the solvents were evaporated off under reduced pressure. The residue from evaporation was purified using silica column chromatography, eluting with a 95/5 (v/v) methylene chloride/methanol mixture. 2 g (yield: 32%) of N-[[4-[2-(1-dimethylamino-2-methyl)propyl]-1-piperidinyl]-1-propyl]-5-methylhexanamide was obtained as an oil. The desired ethanedioate was prepared from this oil in acetone. M Pt=73°–75° C.

EXAMPLE 25

Preparation of the Ethyl Ester of 4-[2-[(1-dimethylamino-2-methyl)propyl]-1-piperidine Butanoic Acid, (Z)-2-butenedioate A mixture of 12 g ($6.5 \times 10^{-2}$ mole) of N,N,β,β-tetramethyl-4-piperidineethanamine, 11.6 ml ($8.10^{-2}$ mole) of ethyl 4-bromobutanoate and 22.4 g of potassium carbonate in 200 ml of acetonitrile was refluxed for 4 hours. After evaporating off the solvents under reduced pressure, the residue was taken up in water. It was extracted with ethyl acetate. The organic phase was washed with water, dried over magnesium sulphate and filtered and the solvents were evaporated off under reduced pressure. After purification by silica column chromatography, eluting with a 9/1 (v/v) methylene chloride/methanol mixture, 11.8 g (yield: 61%) of 4-[2-[(1-dimethylamino-2-methyl)propyl]-1-piperidine butanoic acid ethyl ester was recovered as an oil. The corresponding (Z)-2-butenedioate was prepared from this oil in ethanol. M Pt=122° C.

EXAMPLE 26

Preparation of N-(4-methylpentyl)-4-[2-(1-dimethylamino-2-methyl)propyl]-1-piperidinebutanamide, (E)-2-butenedioate A solution of 4 g ($1.2 \times 10^{-2}$ mole) of 4-[2-[(1-dimethylamino-2-methyl)propyl]-1-piperidine butanoic acid ethyl ester and 9 g ($9.10^{-2}$ mole) of 4-methylpentanamine in 50 ml of methylbenzene was introduced into an autoclave and heated at 200° C. for 96 hours. After evaporating off the methylbenzene under reduced pressure, the residue was purified by silica column chromatography, eluting with a 95/5 (v/v) methylene chloride/methanol mixture. After evaporating the pure fractions under reduced pressure, 3 g (yield: 71%) of N-(4-methylpentyl)-4-[2-(1-dimethylamino-2-methyl)propyl]1-piperidinebutanamide was obtained as an oil. The corresponding (E)-2-butenedioate was prepared from this oil in ethanol. M Pt=140° C.

EXAMPLE 27

Preparation of 1-[(1-undecyl)carbonyl]-N,N,N,β,β-pentamethyl-4-piperidinethanaminium Iodide A solution of 1 g ($0.27 \times 10^{-2}$ mole) of 1-undecanoyl-N,N,β,β-tetramethyl-4-piperidineethanamine, 20 ml of ether and 2 ml of iodomethane was refluxed with stirring. After 15 hours, a further 2 ml of iodomethane was added with a further 3 ml 24 hours thereafter, and the resulting mixture was then further heated for about 8 hours. That mixture was cooled and the precipitate formed was filtered out. 0.9 g (yield: 65%) of a white product was obtained which corresponded with the desired product. M Pt=208° C.

The following products were obtained in analogous manner to that of preparation IX:

EXAMPLE 28

1-(3-phenylpropenoyl)-N,N,β,β-tetramethyl-4-piperidineethanamine, (E)-2-butenedioate M Pt=173°–176° C.

EXAMPLE 29

1-[2-(4-chlorophenoxy)-2,2-dimethyl-ethanoyl]-N,N,β,β-tetramethyl-4-piperidineethanamine, (E)-2-butenedioate M Pt=194° C.

The following products were obtained in the same manner as described for the preparation of Example 1:

EXAMPLE 30

1-[2-(4-chlorophenoxy)-2,2-dimethyl-ethyl]-N,N,β,β-tetramethyl-4-piperidineethanamine, (E)-2-butenedioate M Pt=103° C.

EXAMPLE 31

1-(3-phenylpropenyl)-N,N,β,β-tetramethyl-4-piperidineethanamine, (E)-2-butenedioate M Pt=150° C.

EXAMPLE 32

1-[2-[4-(2-methylpropyl)phenyl]-2-methylethyl]-N,N,β,β-tetramethyl-4-piperidineethanamine, (E)-2-butenedioate M Pt=147°–150° C.

Table I below shows a number of compounds of the invention. The symbols used in this table have the following meanings:

n-Pr: $-CH_2-CH_2-CH_3$
n-$C_{12}$: $-(CH_2)_{11}CH_3$
i-Pr: $-CH(CH_3)_2$

Bn: 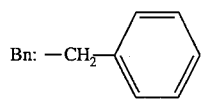

Ph: 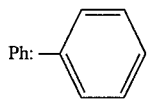

p-ClPh: 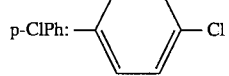

Tbu: $-C(CH_3)_3$

Pht: 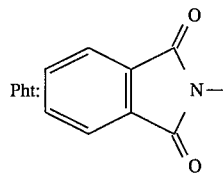

Im: 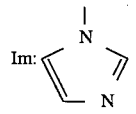

A: 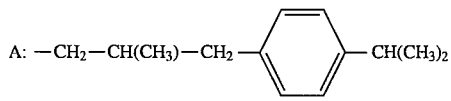

B: $-(CH_2)_3-NH-CO-(CH_2)_3-CH(CH_3)_2$
C: $-(CH_2)_3-CO-NH-(CH_2)_3-CH(CH_3)_2$
D: $-CH_2-CH=CH-C\equiv C(CH_3)_3$ (E)

F: 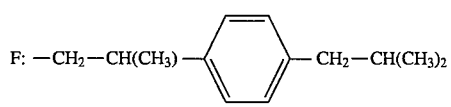

The symbols used for the salts have the following meanings:

oxal: $HO_2C-CO_2H$
Fum: $HO_2C-CH=CH-CO_2H$ (E)
Mal: $HO_2C-CH=CH-CO_2H$ (Z)

TSO₃H: 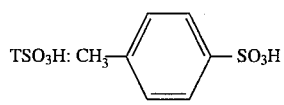

IMA: methylammonium iodide.

The products of the invention are inhibitors for the biosynthesis of cholesterol, in particular inhibitors of epoxysqualene cyclase.

The activity of the Compounds of the invention was evaluated by the observation of an inhibiting effect on epoxysqualene cyclase in the hepatic microsomes of male Wistar rats.

The method consisted of measuring the lanosterol formed from R,S-2,3-oxydosqualene by the microsomal enzyme. The enzyme was prepared using the method described by G. C. Ness (G. C. Ness et. al., Biochem. J., (1986), 233, 167–172).

Method for Measuring the Activity of Epoxysqualene Cyclase

Rat hepatic microsomes were used as the source of the enzyme. The method consisted in measuring the lanosterol formed from (R,S)-2,3-oxydosqualene. The (R,S)-2,3-oxydosqualene, the products to be tested and TWEEN® 80 in organic solution (2-propanone or sulphinyl bis-methane) (25 μl) were placed in test tubes and 400 μl of potassium buffer (0.1M, pH=7.4) was added. The reaction was initiated by adding 100 μl of the microsomes. In a final reaction volume of 525 μl, the mixture contained 150 μM of (R,S)-2,3-oxydosqualene, 0.1% of TWEEN® 80 (to dissolve the (R,S)-2,3-oxydosqualene) and 250 μg of microsomal proteins. The reaction time was 60 minutes at 37° C. The reaction was stopped by addition of 300 μl of methanolic potassium hydroxide (7%) and 20 μg of stigmasterol as an internal standard. After saponification at 80° C. for 30 minutes and stirring using a rotary stirrer, the sterols were extracted with 2 ml of hexane. The lanosterol formed was separated from the (R,S)-2,3-oxydosqualene, the membranal cholesterol and the stigmasterol by gas phase chromatography after transformation to the trimethylsilyl ethers. Derivatisation of the sterols was carried out at 60° C. for 30 minutes after addition of 25 μl of pyridine and 75 μl of the trimethylsilyl ester of 2,2,2-trifluoro-N-trimethylsily-ethanimidic acid containing 1% of trimethylchlorosilane ethers.

After evaporation, the trimethylsilyl ethers were taken up into solution in 100 μl of hexane. An aliquot of this solution (2 μl) was gas chromatographed on a OV1 capillary column (0.32 mm, 25 m) under the following conditions: injection temperature=270° C., furnace temperature=260° C., detector temperature=300° C.; the vector gas was nitrogen at a pressure of $7.10^4$ Pa.

The potency of the molecules tested was expressed as the percentage inhibition of the quantity of lanosterol formed for a concentration of $25.10^{-6}$ moles per liter of product tested. The results obtained with some of the compounds of the invention are shown in Table II.

The products of the invention have therapeutic use in the treatment and prevention of hypercholesterolemia, in particular in the associated phenomena of arterial lesions such as atherosclerosis, and of mycoses and other parasitic infections caused by a fungus such as *Actinomyces mentagro-* phytes, *Candida tropicalis, Candida albicans, Candida glabrata* or *Aspergillus fumigatus*.

In accordance with the invention, a therapeutic composition is provided which comprises at least one compound of the formula I or one of its addition salts in a therapeutically effective amount, in association with a physiologically acceptable excipient.

The use of a compound of the formula I or one of its addition salts as an epoxysqualene cyclase inhibitor is also provided, in order, to obtain a preventative or curative hypocholesterolemic, hypolipemic, antiatheromatic and/or antifungal medicament. Products of the formula I in accordance with the invention and their addition salts are of particular use in the treatment of D.I.C (disseminated intravascular coagulations), in particular those induced by fungi such as *Candida albicans* and *Candida glabrata*.

The best mode for carrying out the invention consists in using the products of Examples 2, 16 and 18 as medicaments, in particular as hypocholesterolemic and/or antifungal agents.

TABLE I (I)

| Ex. | $R_1$ | $R_2$ | $R_3$ | Salt |
|---|---|---|---|---|
| 1 | H | H | n-$C_{12}$ | Fum |
| 2 | $CH_3$ | $CH_3$ | n-$C_{12}$ | 2 Fum |
| 3 | $CH_3$ | Bn | n-$C_{12}$ | Fum |
| 4 | $CH_3CH_2$ | $CH_3$—$CH_2$ | n-$C_{12}$ | 2 Fum |
| 5 | Bn | H | n-$C_{12}$ | 2 Fum |
| 6 | $CH_3$ | H | n-$C_{12}$ | 2 $TSO_3H$ |
| 7 | n-Pr | H | n-$C_{12}$ | 2 Fum |
| 8 | i-Pr | H | n-$C_{12}$ | 2 $TSO_3H$ |
| 9 | $CH_3CH_2$ | H | n-$C_{12}$ | 2 Fum |
| 10 | $CH_3$—CO | $CH_3$ | n-$C_{12}$ | $TSO_3H$ |
| 11 | $CH_3$—CO | H | n-$C_{12}$ | Fum |
| 12 | $CH_3$ | $CH_3$ | $CH_3$ | 2 Fum |
| 13 | $CH_3$ | $CH_3$ | —$CH_2$—CH=$CH_2$ | 2 Mal |
| 14 | $CH_3$ | $CH_3$ | —$CH_2$—CH=C($CH_3$)$_2$ | 2 Fum |
| 15 | * | * | n-$C_{12}$ | 2 Mal |
| 16 | $CH_3$ | $CH_3$ | D | 2 Mal |
| 17 | $CH_3$ | $CH_3$ | $(CH_2)_5$—Tbu | 2 Fum |
| 18 | $CH_3$ | $CH_3$ | A | 2 Fum |
| 19 | $CH_3$ | $CH_3$ | CO—$(CH_2)_{10}$—$CH_3$ | Oxal |
| 20 | $CH_3$ | $CH_3$ | CO—$(CH_2)_{10}$—Im | 2.5 oxal |
| 21 | $CH_3$ | $CH_3$ | $(CH_2)_{11}$—Im | 2.5 Fum |
| 22 | $CH_3$ | $CH_3$ | $(CH_2)_3$—Pht | 2 Fum |
| 23 | $CH_3$ | $CH_3$ | $(CH_2)_3$—$NH_2$ | 2 Fum |
| 24 | $CH_3$ | $CH_3$ | B | 2 oxal |
| 25 | $CH_3$ | $CH_3$ | $(CH_2)_3$—$CO_2$—$CH_2$—$CH_3$ | 2 Mal |
| 26 | $CH_3$ | $CH_3$ | C | 2 Fum |
| 27 | $CH_3$ | $CH_3$ | CO—$(CH_2)_{10}$—$CH_3$ | IMA |
| 28 | $CH_3$ | $CH_3$ | CO—CH=CH—Ph | Fum |
| 29 | $CH_3$ | $CH_3$ | CO—C($CH_3$)$_2$—O-pClPh | Fum |
| 30 | $CH_3$ | $CH_3$ | $CH_2$—C($CH_3$)$_2$—O-pClPh | Fum |
| 31 | $CH_3$ | $CH_3$ | $CH_2$—CH=CH—Ph | 2 Fum |
|  | $CH_3$ | $CH_3$ | F | 2 Fum |

*$R_1$ and $R_2$ form a piperidinyl group with the nitrogen atom to which they are bonded.

TABLE II

| Ex | Inhibition percentage for $25.10^{-6}$ mole of tested product |
|---|---|
| 1 | 75 |
| 2 | 97 |

TABLE II-continued

| Ex | Inhibition percentage for $25.10^{-6}$ mole of tested product |
|---|---|
| 4 | 63 |
| 9 | 96 |
| 10 | 66 |
| 11 | 58 |
| 13 | 64 |
| 14 | 48 |
| 15 | 40 |
| 16 | 100 |
| 17 | 100 |
| 18 | 100 |
| 19 | 100 |
| 20 | 100 |
| 21 | 100 |
| 24 | 93 |
| 25 | 81 |
| 26 | 100 |
| 27 | 100 |
| 28 | 87 |
| 29 | 95 |
| 30 | 92 |
| 31 | 99 |
| 32 | 95 |

We claim:

1. A β,β-dimethyl-4-piperidineethanamine compound, characterised in that it is selected from the group consisting of:

(i) compounds of the formula:

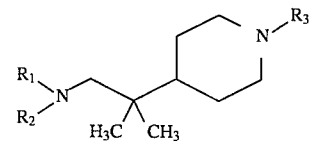

(I)

wherein $R_1$ and $R_2$, which may be identical or different, each represent a hydrogen atom, a $C_1$-$C_4$ alkyl group, a $C_2$-$C_5$ acyl group or a phenylmethyl group, or form a piperidinyl group with the nitrogen atom to which they are bonded, $R_3$ represents
a linear or branched $C_1$-$C_{12}$ alkyl group which may be substituted by:
  a) an imidazolyl group, or
  b) a phenyl group which may itself be substituted by a linear or branched $C_1$-$C_4$ alkyl group,
a linear or branched $C_3$-$C_{10}$ alkyl group containing one or more C=C or C≡C bonds, and which may be substituted by a phenyl group,
a linear or branched $C_1$-$C_4$ alkyloxy group, substituted by a para-chlorophenyl group,
a —CO—$R_8$ group, wherein $R_8$ represents a linear or branched $C_8$-$C_{11}$ alkyl group which may be substituted by an imidazolyl group, a linear or branched $C_1$-$C_4$ alkyloxy group, substituted by a para-chlorophenyl group, or a linear or branched $C_2$-$C_4$ alkyl group containing at least one double bond and substituted by a phenyl group,
a linear or branched $C_1$-$C_4$ alkyl group substituted by one of the following groups:
  a —$COOR_4$ group, wherein $R_4$ represents either a hydrogen atom or a linear or branched $C_1$-$C_4$ alkyl group,
  a 1H-isoindole-1,3(2H)-dione group,
  a $NR_5R_6$ group, wherein $R_5$ and $R_6$, which may be identical or different, each represent a hydrogen atom or a linear or branched $C_1$-$C_4$ alkyl group, a —NH—CO—R₇ group or a —CO—NH—R₇ group wherein R₇ represents a linear or branched $C_1$–$C_6$ alkyl group, and (ii) their addition salts, in particular their acid addition salts and ammonium salts.

2. A compound according to claim 1, wherein in that the addition salt is a salt obtained from an organic or inorganic acid.

3. A compound of the formula I according to claim 1, wherein in that the addition salt is an ammonium salt obtained from a $C_1$–$C_{14}$ alkyl iodide.

4. 1-dodecyl-N,N,β,β-tetramethyl-4-piperidineethanamine, (E)-2-butenedioate.

5. (E)-1-(6,6-dimethyl-2-hepten-4-yn-1-yl)-N,N,β,β-tetramethyl-4-piperidineethanamine, (E)-2-butenedioate.

6. 1-[3-[4-(methylethyl)phenyl]-2-methylpropyl]-N,N,β,β-tetramethyl-piperidineethanamine, (E)-2-butenedioate.

7. A method for the preparation of a compound of the formula I or one of its salts in accordance with claim 1, said method comprising the following steps:

(i) N-alkylating or N-acylating a compound of the formula:

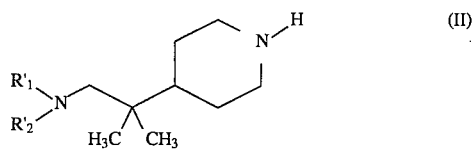

wherein:

$R'_1$ and $R'_2$, which may be identical or different, each represent a hydrogen atom, a $C_1$–$C_4$ alkyl group or a phenylmethyl group, or form a piperidinyl group with the nitrogen atom to which they are bonded, by reaction with a compound of the formula $R'_3$—X wherein X represents a halogen such as a bromine or chlorine atom, and $R'_3$ represents:

a linear or branched $C_1$–$C_{12}$ alkyl group which may be substituted by an imidazolyl group or a phenyl group which may itself be substituted by a linear or branched $C_1$–$C_4$ alkyl group, a linear or branched $C_3$–$C_{10}$ alkyl group containing one or more double or triple bonds, a —CO—$R'_8$ group, wherein $R'_8$ represents a linear or branched $C_8$–$C_{11}$ alkyl group which may be substituted by an imidazolyl group, a linear or branched $C_1$–$C_4$ alkyl group substituted by
a —COOR'₄ group, wherein $R'_4$ represents a hydrogen atom or a linear or branched $C_1$–$C_4$ alkyl group, or a 1H-isoindole-1,3(2H)-dione group, at a molar ratio of 1 mole of compound of the formula II for 1.1 moles of compound of the formula $R'_3$—X, at a temperature of between 0° C. and 200° C. for a period of at least one hour, to obtain a compound of the formula:

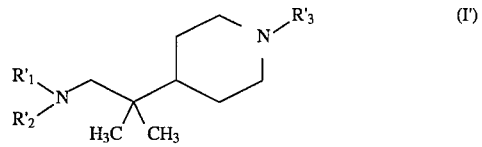

wherein $R'_1$, $R'_2$ and $R'_3$ are as defined above;

(ii) if necessary, carrying out at least one of the following treatments on the compounds of the formula I' thus obtained:

(a) transforming compounds of the formula I' wherein $R'_3$ represents a linear or branched $C_3$–$C_{10}$ alkyl group containing one or more C=C or C≡C bonds and $R'_1$ and $R'_2$ are as defined above, by catalytic hydrogenation in a Parr's apparatus, in an alcohol, in the presence of a catalyst, to compounds of the formula I wherein $R_1$ and $R_2$, which may be identical or different, each represent a hydrogen atom, a linear or branched $C_1$–$C_4$ alkyl group or a phenylmethyl group, or form a piperidinyl group with the nitrogen atom to which they are bonded, and $R_3$ represents a linear or branched $C_3$–$C_{10}$ alkyl chain;

(b) hydrolysing compounds of the formula I' wherein $R'_1$ and $R'_2$ are as defined above and $R'_3$ represents a linear or branched $C_1$–$C_4$ alkyl group substituted by a 1H-isoindole-1,3(2H)-dione group, in the presence of hydrazine hydrate, optionally followed by N-alkylation of the primary amine thus produced, using a $C_1$–$C_4$ alkyl group to produce compounds of the formula I wherein $R_1$ and $R_2$, which may be identical or different, each represent a hydrogen atom, a linear or branched $C_1$–$C_4$ alkyl group or a phenylmethyl group, or form a piperidinyl group with the nitrogen atom to which they are bonded, and $R_3$ represents a linear or branched $C_1$–$C_4$ alkyl group substituted by a $NR_5R_6$ group wherein $R_5$ and $R_6$, which may be identical or different, each represent a hydrogen atom or a linear or branched $C_1$–$C_4$ alkyl group;

c) N-acylating the primary amine thus obtained in step (b) by reaction with an acid halide of the formula X—CO—R₇ wherein X represents a halogen atom and R₇ represents a linear or branched $C_1$–$C_6$ alkyl group, to obtain compounds of the formula I wherein $R_1$ and $R_2$, which may be identical or different, each represent a hydrogen atom, a linear or branched $C_1$–$C_4$ alkyl group or a phenylmethyl group, or form a piperidinyl group with the nitrogen atom to which they are bonded, and $R_3$ represents a linear or branched $C_1$–$C_4$ alkyl group substituted by a —NH—CO—R₇ group wherein R₇ represents a linear or branched $C_1$–$C_6$ alkyl group;

(d) amidifying compounds of the formula I' wherein $R'_1$ and $R'_2$ are as defined above and $R'_3$ represents a linear or branched $C_1$–$C_4$ alkyl group substituted by a —COOR'₄ group, wherein $R'_4$ represents a hydrogen atom or a linear or branched $C_1$–$C_4$ alkyl group, by reaction with a primary amine, to obtain compounds of the formula I wherein $R_1$ and $R_2$, which may be identical or different, each represent a hydrogen atom, a linear or branched $C_1$–$C_4$ alkyl group or a phenylmethyl group, or form a piperidinyl group with the nitrogen atom to which they are bonded, and $R_3$ represents a linear or branched $C_1$–$C_4$ group substituted by a —CO—NH—R₇ group wherein R₇ represents a linear or branched $C_1$–$C_6$ alkyl group;

(e) reducing compounds of the formula I' wherein $R'_1$ and $R'_2$ are as defined above and $R'_3$ represents a —CO—$R'_8$ group, wherein $R'_8$ represents a linear or branched $C_8$–$C_{11}$ alkyl group which may be substituted by an imidazolyl group, in the presence of a reducing agent, then treating with a strong base to obtain compounds of the formula I wherein $R_1$ and $R_2$, which may be identical or different, each represent a hydrogen atom, a $C_1$–$C_4$ alkyl group or a phenylmethyl group, or form a piperidinyl group with the nitrogen atom to which they are bonded, and $R_3$ represents a linear or branched $C_8$–$C_{12}$ alkyl group which may be substituted by an imidazolyl group;

(f) acylating compounds of the formula I' wherein one of the two groups $R'_1$ and $R'_2$ represent a hydrogen atom, the other being a hydrogen atom, a $C_1$–$C_4$ alkyl group or a phenylmethyl group, and $R'_3$ has the meaning given for $R_3$, by reaction with an acid anhydride to obtain compounds of the formula I wherein one of the groups $R_1$ or $R_2$ represents an acyl group, the other being a hydrogen atom, a $C_1$–$C_4$ alkyl group or a phenylmethyl group, and $R_3$ represents a linear or branched $C_1$–$C_{12}$ alkyl group which may be substituted by an imidazolyl group or a phenyl group which may itself be substituted by a $C_1$–$C_4$ alkyl group, a linear or branched $C_3$–$C_{10}$ alkyl group containing one or more double or triple bonds, a —CO—$R_8$ group wherein $R_8$ represents a linear or branched $C_8$–$C_{11}$ alkyl group which may be substituted by an imidazolyl group, a linear or branched $C_1$–$C_4$ alkyl group substituted by:
  a —COO$R_4$ group wherein $R_4$ represents a hydrogen atom or a linear or branched $C_1$–$C_4$ alkyl group,
  a 1H-isoindole-1,3(2H)-dione group,
  a $NR_5R_6$ group wherein $R_5$ and $R_6$, which may be identical or different, each represent a hydrogen atom or a linear or branched $C_1$–$C_4$ alkyl group,
  a —NH—CO—$R_7$ or —CO—NH—$R_7$ group wherein $R_7$ represents a linear or branched $C_1$–$C_6$ alkyl group.

8. An intermediate compound for use in the synthesis of compounds of the formula I according to claim 1, which is represented by the formula:

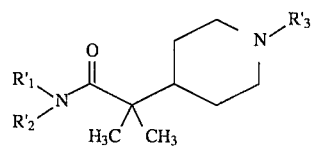

wherein $R'_1$ and $R'_2$, which may be identical or different, each represent a hydrogen atom, a linear or branched $C_1$–$C_4$ alkyl group or a phenylmethyl group, or form a piperidinyl group with the nitrogen atom to which they are bonded, and $R'_3$ represents a linear or branched $C_1$–$C_{12}$ alkyl group or a linear or branched $C_3$–$C_{10}$ alkyl group containing one or more C=C or C≡C bonds.

9. A therapeutic composition, which comprises at least one compound of the formula I as claimed in claim 1 or an addition salt thereof in a therapeutically effective amount, in association with a physiologically acceptable excipient.

10. A method of inhibiting the biosynthesis of cholesterol for the treatment of hypercholesterolemia, atherosclerosis, or mycoses, which comprises administering to a patient in need of such a treatment a therapeutically effective amount of a compound of claim 1.

* * * * *